United States Patent [19]

Sato et al.

[11] Patent Number: 5,099,047
[45] Date of Patent: Mar. 24, 1992

[54] METHOD FOR RECOVERING A GROUP VIII METAL SOLID COMPLEX AND HYDROFORMYLATION METHOD

[75] Inventors: Keiichi Sato, Tokyo; Yuji Kawaragi, Yokohama, both of Japan

[73] Assignee: Mitsubishi Kasei Corporation, Tokyo, Japan

[21] Appl. No.: 611,515

[22] Filed: Nov. 13, 1990

[30] Foreign Application Priority Data

Nov. 17, 1989 [JP] Japan .................................. 1-299429
Nov. 20, 1989 [JP] Japan .................................. 1-301524

[51] Int. Cl.$^5$ ...................... C07F 15/00; C07F 13/00; C07F 17/00
[52] U.S. Cl. ..................................... 556/136; 556/13; 556/16; 556/138; 568/387; 568/429; 568/444
[58] Field of Search .................. 568/7, 456, 444, 387, 568/429; 556/13, 16, 19, 136, 138

[56] References Cited

U.S. PATENT DOCUMENTS 4,199,478  4/1980  Mantovani et al. ............ 568/444 X
4,782,188  11/1988  Butts ................................... 568/444

FOREIGN PATENT DOCUMENTS 49781    4/1982   European Pat. Off. .
156253   10/1985  European Pat. Off. .
354588   2/1990   European Pat. Off. .
2505180  8/1976   Fed. Rep. of Germany .
2085747  5/1982   United Kingdom .

*Primary Examiner*—Arthur C. Prescott
*Attorney, Agent, or Firm*—Oblon, Spivak, McClelland, Maier & Neustadt

[57] ABSTRACT

A method for recovering a Group VIII metal solid complex from an organic compound-containing solution containing a Group VIII metal complex, wherein the Group VIII metal complex is precipitated in the presence of a trialkyl phosphine of the following formula (I):

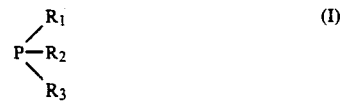

wherein each of $R_1$, $R_2$ and $R_3$ is an alkyl group and they may be the same or different from one another, and the sum of the carbon numbers of $R_1$, $R_2$ and $R_3$ is at least 42.

27 Claims, No Drawings

METHOD FOR RECOVERING A GROUP VIII METAL SOLID COMPLEX AND HYDROFORMYLATION METHOD

The present invention relates to a method for economically and efficiently recover a Group VIII metal solid complex from an organic compound-containing solution containing a Group VIII metal complex. The present invention also relates to an industrially advantageous hydroformylation method wherein the above recovery of the Group VIII metal solid complex is employed.

Heretofore, a soluble complex of a compound of a metal of Group VIII of the Periodic Table and an organic phosphorus compound has been used as a catalyst for various reactions such as a hydrogenation reaction, a carbonyl-modification reaction and oligomerization. Further, it is common to employ a soluble complex of a Group VIII metal compound and an organic phosphorus compound in a hydroformylation method for producing an aldehyde or an alcohol as its hydrogenated product, by reacting an olefinic compound with water gas in the presence of a catalyst. In these reactions, the catalyst is in a state uniformly dissolved in the reaction solution. Therefore, it is important economically and from the viewpoint of preventing environmental pollution to separate and recover the catalyst efficiently from the solution withdrawn after the reaction. It is common to employ distillation separation as a method for separating and recovering a Group VIII metal complex from the reaction solutions obtained by the above-mentioned respective reactions. The distillation is effective particularly when the reaction product has a low boiling point, and after separating the reaction product and the catalyst solution, the catalyst can be recycled for reuse to the next reaction in an active form. However, when the heat resistance of the reaction product is poor, the distillation for separation can not be employed.

Further, the above-mentioned complex is usually not stable against high temperature heating. Accordingly, when the catalyst is distilled and separated from the high boiling point reaction product, it undergoes thermal degradation, whereby the catalytic activities tend to deteriorate. Therefore, an additional step including a special apparatus or a treatment is required for its regeneration.

More specifically, for example, if the reaction product obtained by the hydroformylation reaction is of a relatively low boiling point, it is usually possible to separate the reaction product from the catalyst solution by distillation, and the catalyst solution can be recycled to the reaction system for reuse However, in the hydroformylation reaction, various high boiling point substances are produced as byproducts. Accordingly, by the recycling of the catalyst solution, such high boiling point byproducts tend to accumulate in the reaction system, whereby it becomes difficult to continue the operation under a stabilized condition. Therefore, it is necessary to remove the high boiling point byproducts from the catalyst solution by e.g. distillation. However, if the distillation is conducted at a high temperature, the above complex undergoes thermal degradation, and the activities of the recycled catalyst tend to deteriorate.

When the hydroformylation product has a high boiling point, the activities of the recycled catalyst tend to deteriorate in the same manner as described above.

Accordingly, in order to solve these problems, it becomes necessary to recover the Group VIII metal complex by a method such as adsorption or extraction. For this purpose, the following methods have been, for example, proposed.

(1) Japanese Examined Patent Publication No. 43219/1971 discloses a method which comprises adding a strong acid to a catalyst solution containing a rhodium metal complex to extract the rhodium complex with the strong acid, conducting phase separation to obtain an acid solution containing the rhodium complex, diluting the acid solution with water, whereupon the rhodium complex precipitates, extracting the rhodium complex with a solvent to recover the rhodium complex from said aqueous acid solution.

(2) Japanese Examined Patent Publication No. 3994/1978 discloses a method which comprises adding an organic solution containing a Group VIII metal complex to active carbon treated with nitric acid and permitting the active carbon to adsorb the Group VIII metal complex in the presence of methanol, followed by calcining to recover the Group VIII metal.

(3) Journal of the American Oil Chemical Society, 54, 276-278 (1977) discloses a method of using an aqueous HCN solution containing triethanolamine as an extracting agent for extracting a rhodium metal complex from the hydroformylation reaction solution obtained by the hydroformylation of e.g. methyl oleate.

(4) A reaction product solution obtained by hydroformylating methyl oleate in the presence of triphenyl phosphite and a rhodium catalyst supported on an alumina carrier, is separated by an filtration operation into an alumina carrier and a filtrate, and the filtrate is separated by distillation into the product and the soluble rhodium catalyst. The separated soluble rhodium catalyst is supported on the alumina carrier and activated by baking, and then it is reused for the hydroformylation reaction. (Journal of American Oil Chemical Society, 50, 455-458 (1973))

(5) An unsaturated fatty acid compound is hydroformylated in the presence of a catalyst comprising a Group VIII metal-organic phosphorus compound complex, and the obtained reaction solution is contacted with an active carbon adsorbent carrying an organic phosphorus compound to adsorb the complex. Then, the complex adsorbed on the adsorbent is eluted by contact with an eluting liquid. On the other hand, the freed organic phosphorus compound is recovered by distillation from the reaction solution after the adsorbing treatment, and it is combined with the complex eluted as mentioned above for reuse in the hydroformylation reaction. (Japanese Unexamined Patent Publication No. 196537/1988)

However, the extraction method by means of a strong acid as described in above item (1), has a problem of corrosion of the apparatus, since the acid (e.g. sulfuric acid of at least 60% by weight) is used. Further, the recovered rhodium complex contains sulfuric acid ions ($SO_4^{2-}$), chlorine ions ($Cl^-$). This sulfur (S) or chlorine (Cl) acts as a catalyst poison to the rhodium complex catalyst and is required to be removed by alkali treatment.

The method of adsorbing on active carbon as disclosed in above item (2) requires a calcination step as a post treating step, whereby a loss of the Group VIII metal to some extent is unavoidable, thus leading to an increase of the production cost.

The extraction method as disclosed in above item (3) is disadvantages in that the extraction rate of the complex is not high and that a toxic extracting agent is used, thus leading to a problem for safety.

The method of above item (4) is hardly applicable on an industrial scale, since the organic phosphorus compound added as a ligand can not be recovered, the recovery operation is cumbersome and with respect to the hydroformylation reaction itself, in order to conduct the hydroformylation reaction at a proper reaction rate and yield, a large amount of rhodium is required, such being industrially disadvantageous.

In the method of above item (5), the freed organic phosphorus compound is required to be recovered by distillation, whereby the operation is cumbersome and uneconomical.

Further, Japanese Unexamined Patent Publications No. 121793/1974, No. 63388/1976, No. 3995/1978 and No. 26218/1979 propose methods for recovery of a Group VIII metal complex. However, they are hardly applicable on an industrial scale in view of the inadequate recovery rate or the cumbersomeness of the process.

The present inventors have conducted extensive researches for a method of a recovering a Group VIII metal complex in an organic compound-containing solution efficiently by a simple operation as a complex active for the above-mentioned reaction, and as a result, have arrived at the present invention. They have further found that the above recovery of the Group VIII metal solid complex can be applied to a hydroformylation reaction solution, whereby the hydroformylation reaction can be conducted industrially advantageously.

Thus, in the broadest sense, the present invention provides a method for recovering a Group VIII metal solid complex from an organic compound-containing solution containing a Group VIII metal complex, wherein the Group VIII metal complex is precipitated in the presence of a trialkyl phosphine of the following formula (I):

wherein each of $R_1$, $R_2$ and $R_3$ is an alkyl group and they may be the same or different from one another, and the sum of the carbon numbers of $R_1$, $R_2$ and $R_3$ is at least 42.

Now, the present invention will be described in detail with reference to the preferred embodiments.

The Group VIII metal complex to be recovered by the method of the present invention is a complex containing at least one metal selected from the group consisting of iron, cobalt, nickel, ruthenium, rhodium, palladium, osmium, iridium and platinum and being soluble in an organic compound-containing solution As will be described hereinafter, this complex can be precipitated and separated from the organic compound-containing solution by forming a complex with a specific trialkylphosphine used in the present invention. Accordingly, it is preferred that at least one exchangeable ligand is coordinated on the complex, so that it can readily form a complex with the specific trialkylphosphine, whereby the present invention can effectively be conducted.

Such ligands include, for example, phosphines such as triphenylphosphine, tri-p-tolylphosphine, tris-(m-methoxyphenyl)phosphine, tris(m-chlorophenyl)phosphine, tris(4-dimethylaminophenyl)phosphine, diphenylisopropylphosphine, triethylphosphine, tributylphosphine, tricyclohexylphosphine, tribenzylphosphine and trialkylphosphines of the formula (I), phosphites such as triphenylphosphite, tricyclohexylphosphite, triethylphosphite, trioctylphosphite and tris(2-dimethylaminoethyl)phosphite, olefins such as 1,5-cyclooctadiene, norbornadiene and cyclopentadiene, such as benzonitrile, acetonitrile and acrylonitrile, isonitriles such as t-butylisonitrile, cycloalkylisonitriles (such as cyclohexylisonitrile) and phenylisonitrile, nitrogen-containing compounds such as ethylene diamine, $\alpha,\alpha'$-bipyridyl, 1,10-phenanthroline and pyridine, $\beta$-diketones such as acetyl acetone and benzoyl acetone, $\beta$-ketoesters such as acetoacetate and trifluoroacetoacetate, and carbon monoxide.

Specific examples of the Group VIII metal complex include, for example, $Fe(CO)_5$, $Ni(CO)_4$, $Co(CO)_8$, $RuCl_2(PPh_3)_3$, $Rh_4(CO)_{12}$, $Rh(acac)(CO)_2$, $RhH(CO)(PPh_3)_3$, $PdCl_2(COD)$, $Pd(OAc)_2$, $PtCl_2(PhCN)_2$, $PtCl_2(PPh_3)_2$, $Ir_4(CO)_{12}$ and $OsCl_3\cdot(PEt_3)_3$ where Ph represents a phenyl group, acac represents an acetyl acetonate group, Ac represents an acetyl group and COD represents 1,5-cyclooctadiene. However, the Group VIII metal complex is not limited to such specific examples.

Particularly, the present invention is directed also to a treatment of a soluble complex formed by the reaction using a Group VIII metal complex as a catalyst, and it is advantageously applicable to the recovery of the Group VIII metal complex from the solution withdrawn from the reaction system or from a catalyst solution obtained by further concentrating such withdrawn solution by e.g. distillation.

There is no particular restriction as to the concentration of the Group VIII metal complex dissolved in the organic compound-containing solution, so long as it is uniformly dissolved. However, the concentration is usually selected within a range of from 1 mg to 100 g, preferably from 10 mg to 10 g, per liter of the solution, as calculated by weight of the metal atoms.

As mentioned above, the present invention comprises precipitating the solid complex of the Group VIII metal in the presence of a specific trialkylphosphine in the organic compound-containing solution containing the Group VIII metal complex.

As such a trialkylphosphine, a trialkylphosphine of the formula (I):

wherein each of $R_1$, $R_2$ and $R_3$ is an alkyl group and they may be the same or different from one another, and the sum of the carbon numbers of $R_1$ $R_2$ and $R_3$ is at least 42, is employed.

Among them, a trialkylphosphine wherein each of the three alkyl groups for $R_1$, $R_2$ and $R_3$ has at least 10 carbon atoms, is preferred. More preferred is a trialkylphosphine wherein each of the three alkyl groups has the same carbon number. Further, it is particularly preferred that each of the three alkyl groups has at least 16 carbon atoms. If the total carbon number of the alkyl groups is less 42, the recovery rate of the solid complex of the Group VIII metal tends to be poor.

The upper limit of the sum of the carbon numbers of the three alkyl groups for $R_1$, $R_2$ and $R_3$ is not particularly limited. However, it is unnecessary to increase the carbon numbers beyond the levels where the present invention can be conducted efficiently. Usually, the sum of the carbon numbers is at most 90, preferably at most 70.

Specific examples of the trialkylphosphine compound to be used in the present invention includes tri-n-tetradecylphosphine, tri-n-pentadecylphosphine, tri-n-hexadecylphosphine, tri-n-octadecylphosphine, tri-n-eicosylphosphine, tri-n-docosylphosphine, di-n-dodecyl-n-octadecylphosphine, di-n-tetradecyl-n-octadecylphosphine and di-n-hexadecyl-n-decylphosphine. Preferably, tri-n-hexadecylphosphine, tri-n-octadecylphosphine or tri-n-eicosylphosphine is used.

There is no particular restriction as to the amount of the trialkylphosphine to be used, and the amount may optionally be determined so that the Group VIII metal complex can be recovered at a high recovery rate. Usually, the amount is at least about 1 mol, preferably at least 3 mols, per gram atom of the Group VIII metal.

For the precipitation operation, it is not essential to use a poor solvent. However, in order to increase the precipitation rate of the Group VIII metal solid complex, it is preferred to use a solvent inert to the complex. Preferred examples of such poor solvent include methanol, ethanol, propanol, n-butyl alcohol, acetonitrile and dimethylformamide.

The precipitation treatment can be conducted properly by using a known precipitation apparatus and employing one step precipitation or multi-step precipitation. The precipitation temperature is not particularly limited so long as the Group VIII metal complex and the organic compound-containing solution can be separated, but the precipitation is operated usually within a range of from −78° to 80° C., preferably from −20° C. to 50° C.

The precipitated Group VIII metal solid complex is usually subjected to solid-liquid separation by a usual solid-liquid separation method such as filtration, centrifugal filtration or centrifugal separation to obtain the Group VIII metal solid complex.

The recovered Group VIII metal solid complex may be by itself or after subjecting it to proper regeneration treatment, reused as an active soluble complex catalyst for the above-mentioned various reactions.

For example, when the reaction zone is the one wherein the specific trialkylphosphine of the formula (I) is employed, the solution withdrawn from the reaction system is subjected to the above-mentioned precipitation treatment, and the Group VIII metal solid complex thereby separated and recovered is recycled for reuse for the subsequent reaction.

When the reaction is conducted by means of the Group VIII metal alone, as will be described in the Examples given hereinafter, a specific trialkylphosphine of the formula (I) is added to the solution withdrawn from the reaction system, followed by precipitation treatment to recover the Group VIII metal solid complex, which is further subjected to known oxidation treatment such as air oxidation or oxidation by an organic peroxide in order to return the complex to a form active for the reaction, and then the complex is recycled for use for the subsequent reaction.

Further, when the reaction zone is the one wherein a triarylphosphine such as triphenylphosphine is employed, a specific trialkylphosphine of the formula (I) is added to the solution withdrawn from the reaction system, to form a Group VIII metal-trialkylphosphine complex by the ligand exchange, and the Group VIII metal solid complex is recovered by precipitation treatment and then subjected to an oxidation treatment as described above. The triarylphosphine recovered separately by a known method is added thereto, and the mixture is recycled for use for the subsequent reaction.

Further, in the present invention, the above described recovery of the Group VIII metal solid complex is applied to a hydroformylation reaction solution, so that the hydroformylation reaction of an olefinic compound can advantageously be conducted on an industrial scale.

Namely, the present invention provides a hydroformylation method for producing a hydroformylated product by reacting an olefinic compound with carbon monoxide and hydrogen in the presence of a Group VIII metal complex catalyst, wherein at least a part of the hydroformylation reaction solution is withdrawn and subjected to precipitation treatment in the presence of a trialkylphosphine with the sum of the carbon numbers of the alkyl groups being at least 42, to precipitate, separate and recover the Group VIII metal complex catalyst, which is recycled to the hydroformylation reaction zone.

The olefinic compound is not particularly limited so long as it is an organic compound having at least one olefinic double bond in its molecule. Specifically, olefinic hydrocarbons such as ethylene, propylene, butene, butadiene, pentene, hexene, hexadiene, octene, octadiene, decene, hexadecene, octadecene, eicosene, docosene, styrene, α-methylstyrene, cyclohexene as well as olefin oligomer isomer mixtures of dimers to tetramers of lower olefins such as propylene, n-butene and isobutylene, and substituted olefins such as acrylonitrile, allyl alcohol, 1-hydroxy-2,7-octadiene, 3-hydroxy-1,7-octadiene, oleyl alcohol, 1-methoxy-2,7-octadiene, 7-octene-1-al, vinyl acetate, 1-acetoxy-2,7-octadiene, methyl acrylate, methyl methacrylate, methyl oleate and 3-methyl-3-buten-1-ol, may be mentioned. It is a feature of the present invention that the present invention is applicable even when the hydroformylation reaction product obtained by using the above olefin will have a high boiling point as high as at least 160° C. or even when the olefin starting material is poor in the heat stability.

At least a part of the hydroformylation reaction solution is withdrawn and subjected to precipitation treatment in the presence of a trialkylphosphine.

As the trialkylphosphine, the trialkylphosphine of the above formula (I) is employed. Preferred is a trialkylphosphine wherein each of the three alkyl groups for $R_1$, $R_2$ and $R_3$ has at least 10 carbon atoms, and particularly preferred is the one wherein each of the three alkyl groups has at least 16 carbon atoms.

If the total carbon number of the three alkyl groups for $R_1$, $R_2$ and $R_3$ is less than 42, the recovery rate of the solid complex of the Group VIII metal tends to be poor.

The upper limit of the carbon number is not particularly limited. However, it is unnecessary to increase the carbon number beyond a level where the present invention can efficiently be conducted. If the carbon number is too large, the solubility under the hydroformylation reaction condition tends to be low, and it is properly selected so that the reaction solution will be a uniform solution under the hydroformylation reaction condition. The upper limit is usually at most 90, more preferably at most 70.

Specific examples of the organic phosphorus compound include, for example, tri-n-tetradecylphosphine, tri-n-pentadecylphosphine, tri-n-hexadecylphosphine, tri-n-octadecylphosphine, tri-n-eicosylphosphine, tri-n-docosylphosphine, di-n-dodecyl-n-octadecylphosphine, di-n-tetradecyl-n-octadecylphosphine and di-n-hexadecyl-n-decylphosphine. Preferably, tri-n-hexadecylphosphine, tri-n-octadecylphosphine or tri-n-eicosylphosphine is used.

There is no particular restriction as to the amount of the trialkylphosphine to be used. As described hereinafter, when used in a hydroformylation reaction system, the amount is optionally determined in consideration of the activities of the catalyst so that a desired result can be obtained for the recovery of the Group VIII metal complex. The amount is selected usually within a range of from about 0.5 to 500 mols, preferably from 1 to 100 mols, more preferably from 3 to 30 mols per gram atom of the Group VIII metal.

As mentioned above, the Group VIII metal complex used as a catalyst may be any complex containing a Group VIII metal and being soluble in the hydroformylation reaction medium, and specific examples may be the same as mentioned above. Such a complex can be prepared by a known method for forming a complex, or it may be formed in the hydroformylation reaction zone.

Accordingly, even when the Group VIII metal complex catalyst for the hydroformylation reaction does not have an organic phosphorus compound of the formula (I) as a ligand, it is possible that a trialkylphosphine of the formula (I) is reacted to the solution withdrawn from the hydroformylation reaction to precipitate, separate and recover the Group VIII metal solid complex, which can be recycled to the hydroformylation reaction zone again, if necessary, after subjecting it to a suitable regeneration treatment.

When a Group VIII metal complex having the above specific trialkylphosphine as a ligand is to be employed, such a complex can readily be prepared by a known method for forming a complex from a compound of a Group VIII metal, such as a hydride, a halide, an organic salt, an inorganic salt, an oxide, a carbonyl compound or an amine compound and the trialkylphosphine. In some cases, the Group VIII metal compound and the above trialkylphosphine may be supplied to the hydroformylation reaction zone, so that the complex can be formed in the reaction zone.

The Group VIII metal compound includes, for example, ruthenium compounds such as ruthenium trichloride, tetraamine hydroxochlororuthenium chloride and dichlorotris(triphenylphosphine)ruthenium, palladium compounds such as palladium acetate and palladium chloride, osmium compounds such as osmium tetrachloride, iridium compounds such as iridium trichloride and iridium carbonyl, platinum compounds such as platinic acid, sodium hexachloroplatinate and potassium platinate, cobalt compounds such as dicobalt octacarbonyl and cobalt stearate and rhodium compounds such as rhodium tetrachloride, rhodium nitrate, rhodium acetate, $Rh(acac)(CO)_2$, $[Rh(OAc)(COD)]_2$, $Rh_4(CO)_{12}$, $HRh(CO)(PPh_3)_3$ and $[Rh(\mu\text{-StBu})(CO)_2]_2$, wherein acac represents an acetyl acetonate group, Ac represents an acetyl group, COD represents 1,5-cyclooctadiene, Ph represents a phenyl group, and tBu represents a tert-butyl group. However, the Group VIII metal compound is not limited to such specific examples.

The amount of the Group VIII metal compound to be used is not particularly limited. From the viewpoint of the catalytic activities and economical feasibility, however, there is a limit. Usually, the concentration in the hydroformylation reaction zone is selected within a range of from 0.05 mg to 5 g, preferably from 0.5 mg to 1 g, per liter of the olefinic compound, as calculated by the metal atoms.

For the hydroformylation reaction, use of a solvent for the reaction is not essential. If necessary, however, the hydroformylation reaction may be conducted in the presence of an inert solvent. Specific examples of a preferred solvent include aromatic hydrocarbon compounds such as toluene, xylene and dodecylbenzene, ketone, ethers such as tetrahydrofuran and dioxane, and esters such as ethyl acetate and di-n-octylphthalate.

The reaction conditions for the hydroformylation method may be the same as those commonly used in the conventional hydroformylation method. Namely, the reaction temperature is selected usually within a range of from room temperature to 200° C., preferably from 50° to 150° C. The reaction pressure is selected usually within a range of from atmospheric pressure to 200 atm, preferably from 5 to 100 atm, more preferably from 5 to 50 atm. The molar ratio of hydrogen to carbon monoxide ($H_2/CO$) is selected usually within a range of from 10/1 to 1/10, preferably from 1/1 to 6/1. The reaction system for the hydroformylation reaction may be a continuous system or a batch system in a stirring type reactor or an air bubble tower type reactor.

In the present invention, at least a part of the reaction solution from the hydroformylation reaction is withdrawn and subjected to precipitation treatment to precipitate, separate and recover the Group VIII metal complex catalyst, which is then recycled to the hydroformylation reaction zone.

For example, the hydroformylation reaction solution containing the Group VIII metal complex flowing out of the reactor of the above-mentioned hydroformylation reaction, or the one having the concentration of the Group VIII metal complex in the reaction solution increased by a level of from 1 mg to 100 g, preferably from 10 mg to 10 g, per liter of the solution, as calculated by weight of the metal atoms, by removing the formed aldehyde or part of the reaction solvent therefrom by a known method such as distillation, is subjected to precipitation treatment.

Namely, the Group VIII metal complex catalyst is separated and recovered by the precipitation treatment utilizing the solubility of the complex of the trialkylphosphine having the above-mentioned specific carbon numbers and the Group VIII metal in the hydroformylation reaction solution. At that time, the free trialkylphosphine can be precipitated along with the precipitation of the Group VIII metal complex, and it can simultaneously be separated and recovered. For the precipitation treatment, it is preferred to use a poor solvent inert to the catalyst, since it is thereby possible to increase the precipitation rate. Suitable examples of such a poor solvent include methanol, ethanol, propanol, n-butyl alcohol, acetonitrile and dimethylformamide.

The precipitation treatment can be properly conducted using a known precipitation apparatus by means of either one step precipitation method or a multi step precipitation method. The precipitation temperature is not particularly limited so long as the separation of the catalyst from the reaction solution is possible. However, the precipitation is conducted usually within a range of from −78° C. to 80° C., preferably from −20 to 50° C.

The precipitated Group VIII metal complex catalyst can be separated and recovered from the reaction solution by a usual solid-liquid separation method such as filtration, centrifugal filtration or centrifugal separation.

The above precipitation treatment and the separation and recovery of the precipitated solid complex are conducted in an inert gas atmosphere such as nitrogen or argon to prevent the oxidation of the trialkylphosphine, since the trialkylphosphine is susceptible to oxidation in the presence of oxygen to a trialkylphosphine oxide.

The recovered Group VIII metal complex catalyst is recycled to the hydroformylation reaction zone and reused as a catalyst, after subjecting it to purification treatment such as recrystallization, or after subjecting it to a treatment such as ligand exchange, or without As described in detail in the foregoing, according to the method of the present invention, the useful and valuable Group VIII metal complex catalyst can be separated and recovered selectively and in good yield by simple treatments such as precipitation treatment and solid-liquid separation treatment from the hydroformylation reaction solution. At the same time, the free trialkylphosphine can simultaneously be separated and recovered. The recovered catalyst can be reused for the hydroformylation reaction. Thus, the industrial value of the present invention is significant.

Now, the present invention will be described in further detail with reference to Examples. However, it should be understood that the present invention is by no means restricted by such specific Examples.

99% of rhodium was found to be recovered as the solid complex.

EXAMPLE 2

The operation was conducted in the same manner as in Example 1 except that instead of $(n-C_{18}H_{37})_3P$, an equimolar amount of $(n-C_{16}H_{37})_3P$ was used, whereby 98.1% of rhodium was recovered as the solid complex.

COMPARATIVE EXAMPLE 1

The operation was conducted in the same as in Example 1 except that instead of $(n-C_{18}H_{37})_3P$, an equimolar amount of $(n-C_{12}H_{25})_3P$ was used, whereby no rhodium complex precipitated even after precipitation treatment for 2 hours.

EXAMPLES 3 to 6

The operation was conducted in the same manner as in Example 1 except that instead of $Rh(acac)(CO)_2$, the Group VIII metal complex as identified in Table 1 was used in the amount as identified in Table 1. The recovery rate of each metal obtained as the solid complex after the precipitation operation is shown in Table 1.

COMPARATIVE EXAMPLES 2 to 5

The operation was conducted in the same manner as in Example 1 except that instead of $Rh(acac)(CO)_2$ complex, the Group VIII metal complex as identified in Table 1 was used in the amount as identified in Table 1, and instead of $(n-C_{18}H_{37})_3P$, an equimolar amount of $(n-C_{12}H_{25})_3P$ was used.

As shown in Table 1, in each case, no complex precipitated.

TABLE 1

| Example No. | Group VIII metal complex Type | Amount (mg) | Trialkylphosphine | P/Group VIII metal (atomic ratio) | Recovery rate of metal (%) |
|---|---|---|---|---|---|
| Example 3 | $PdCl_2(COD)$ | 10.6 | $(n-C_{18}H_{37})_3P$ | 6.8 | 100 |
| Example 4 | $Co_2(CO)_8$ | 6.3 | | 6.6 | 100 |
| Example 5 | $PtCl_2(PhCN)_2$ | 18.1 | | 6.0 | 99 |
| Example 6 | $RuCl_2(PPh_3)_3$ | 38.2 | | 6.1 | 99 |
| Comparative Example 2 | $PdCl_2(COD)$ | 10.4 | $(n-C_{12}H_{25})_3P$ | 5.2 | 0 |
| Comparative Example 3 | $Co_2(CO)_8$ | 6.3 | | 6.6 | 0 |
| Comparative Example 4 | $PtCl_2(PhCN)_2$ | 18.1 | | 4.9 | 0 |
| Comparative Example 5 | $RuCl_2(PPh_3)_3$ | 38.7 | | 4.7 | 0 |

EXAMPLE 1

Into a glass test tube having an internal capacity of 50 ml, 10 ml of benzene, 9.6 mg of $Rh(acac)(CO)_2$ and 196.0 mg of $(n-C_{18}H_{37})_3P$ were charged under an argon atmosphere, heated and stirred to obtain a uniform solution. Then, to this solution, 40 ml of deaerated methanol was added, and the mixture was cooled to a temperature of from 5° to 8° C., whereby a rhodium complex started to precipitate. The mixture was maintained in this state for 2 hours, whereupon the precipitate was subjected to filtration under the reduced pressure by means of a 0.8 μ membrane filter for solid-liquid separation. The precipitate was further dried under vacuum at room temperature to obtain a beige solid complex.

With respect to the filtrate after the precipitation, rhodium analysis was conducted by means of a Zeeman type atomic absorption measuring device, whereby the amount of dissolved rhodium was found to be 1.0% relative to the amount of charged rhodium. Namely,

EXAMPLE 7

Into a stainless steel spinner agitation type microautoclave having an internal capacity of 70 ml, 27 ml of methyl oleate crude raw material (85.34 wt % of methyl oleate, 11.29 wt % of methyl stearate, 0.17 wt % of methyl hexadecanoate, 2.66 wt % of methyl palmitate, and not more than 0.2 wt % of methyl linolate), 3 ml of n-tetradecane, 14.7 mg of $Rh(acac)(CO)_2$ and 6 mols, per mol of rhodium, of $(n-C_{18}H_{37})_3P$ were charged under an argon atmosphere, and then the autoclave was closed. Further, argon gas was injected to a pressure of 5 kg/cm²G, followed by returning the pressure to atmospheric pressure, and this operation was repeated three times. Then, the temperature was raised to 130° C. After the temperature reached 130° C., water gas $(H_2/CO=1)$ was immediately injected to a pressure of 7.5 kg/cm²G to initiate the reaction, and the reaction was continued for 5 hours.

During the reaction, consumed water gas was supplemented from a pressure container via a secondary pressure controlling device, so that the reaction pressure was maintained at a constant level of 7.5 kg/cm²G.

After the reaction, the reaction solution was withdrawn to a Schlenk tube under an argon atmosphere, and a part thereof was subjected to gas chromatography (column: Thermon-3000 capillary: 0.25φ×50 m) to measure the concentrations of the products. The conversion of the methyl oleate (hereinafter referred to simply as "MO") and methyl linolate (hereinafter referred to simply as "ML") were 88.2 mol %, and the yield of methylformyl stearate (hereinafter referred to simply as "MFS") was 86.3 mol %, and the yield of methyl stearate (hereinafter referred to simply as "MS") was 1.1 mol %.

Then, to the reaction solution thus obtained, methanol deaerated with argon was added in an amount of four times by volume relative to the reaction solution, and the mixture was cooled to a temperature of from 4° to 5° C., whereby a rhodium complex started to precipitate. The mixture was maintained in this state for 2 hours, and then precipitate was subjected to filtration under reduced pressure by means of a 0.2μ membrane filter for solid-liquid separation. With respect to the filtrate after the precipitation treatment, the rhodium analysis was conducted by means of a Zeeman type atomic absorption measuring device, whereby dissolved rhodium was found to be 0.06% relative to the charged rhodium. This means that 99.9% of rhodium was recovered as the solid complex. On the other hand, the recovered solid complex was vacuum-dried at room temperature, and then 27 ml of the above-mentioned methyl oleate raw material and 3 ml of n-tetradecane were added thereto under an argon atmosphere. Then, the second reaction was conducted in the same manner as the above-mentioned first reaction. The results of the gas chromatography analysis of the solution withdrawn from the reaction system were as follows: (MO+ML) conversion: 91.3%, MFS yield: 89.6%, and MS yield: 1.2%. The reaction solution was subjected to solid-liquid separation in the same manner as the above-mentioned precipitation treatment, and then the rhodium analysis was conducted with respect to the filtrate, whereby dissolved rhodium was found to be 0.59% relative to the charged rhodium. This means that 99.4% of rhodium was recovered as the solid complex.

COMPARATIVE EXAMPLE 6

The first hydroformylation reaction was conducted in the same manner as in Example 7 except that instead of $(n-C_{18}H_{37})_3P$, $(n-C_{12}H_{25})_3P$ was used. The results of the gas chromatography analysis of the solution withdrawn after the reaction were as follows: (MO+ML) conversion: 90.3 mol %, MFS yield: 88.5 mol %, and MS yield: 1.3 mol %. In the same manner in Example 1, precipitation and separation of the rhodium complex were attempted by the same precipitation treatment as in Example 1, but the complex did not precipitate at all.

EXAMPLE 8

The hydroformylation reaction and the precipitation treatment were conducted in the same manner as in Example 7 except that the hydroformylation reaction was conducted for three hours by using, instead of methyl oleate, the same amount by volume of 1-octene (purity: at least 99%) and acetonitrile was used as the solvent added for the precipitation operation. The results of the first hydroformylation reaction were as follows: octene conversion: 94.7 mol %, and nonylaldehyde yield: 94.1 mol %. The recovery rate of rhodium after the precipitation treatment was 99.6% relative to the amount of charged rhodium. Further, the result of the second hydroformylation reaction using the above recovered rhodium complex were as follows: octene conversion: 94.0 mol %, and nonylaldehyde yield: 93.5 mol %. Further, the recovery rate of rhodium by the precipitation treatment was 99.8% relative to the charged rhodium.

COMPARATIVE EXAMPLE 7

The first hydroformylation reaction was conducted in the same manner as in Example 8 except that instead of $(n-C_{18}H_{37})_3P$, $(n-C_{12}H_{25})_3P$ was used. The results of the reaction were as follows: octene conversion: 92.9 mol %, and nonylaldehyde yield: 92.0 mol %. Precipitation and separation of the rhodium complex was attempted by the same precipitation treatment as in Example 8, but the complex did not precipitate at all.

EXAMPLE 9

Into a stainless steel top and bottom agitation type autoclave having an internal capacity of 200 ml, 50 ml of 3-methyl-3-buten-1-ol (hereinafter referred to simply as "IPEA"), 5 ml of toluene, 13.2 mg of $Rh(acac)(CO)_2$ and 4 mols, per mol of rhodium atom, of $(n-C_{18}H_{37})_3P$ were charged under a nitrogen atmosphere. The interior of the autoclave was substituted three times with 10 kg/cm²G of nitrogen gas. Then, the pressure was returned to atmospheric pressure, and the temperature was raised to 120° C. After the temperature reached 120° C., water gas ($H_2/CO=1$) was injected to a total pressure of 30 kg/cm²G to initiate the reaction, and the reaction was continued for 4 hours while maintaining the reaction pressure at a level of 30 kg/cm²G. The results of the gas chromatography analysis (column: Thermon-3000 capillary: 0.25φ×50 m) after the reaction are shown in Table 2. Then, to the total amount of this reaction solution, the precipitation treatment was conducted in the same manner as in Example 1 except that 200 ml of acetonitrile was added instead of methanol as a poor solvent, and the mixture was cooled to 0° C. and maintained at that temperature for 3 hours. The recovery rate of rhodium is shown in Table 2.

Then, using the total amounts of the rhodium complex and free $(n-C_{18}H_{37})_3P$ recovered by the precipitation, the hydroformylation reaction of IPEA and the precipitation treatment were conducted under the same conditions as the above described first reaction. The results are shown in Table 2.

TABLE 2

|  | Conversion of IPEA (mol %) | Yields of products*¹ (mol %) | | | Recovery rate of Rh*² (%) |
| --- | --- | --- | --- | --- | --- |
|  |  | IVA | 2-IPEA | HMTP |  |
| First reaction | 91.2 | 4.4 | 2.7 | 81.9 | 99.4 |
| Recycle reaction | 90.7 | 3.8 | 2.9 | 82.6 | 99.3 |

*¹IVA: Isovaleraldehyde
2-IPEA: 3-Methyl-2-buten-1-ol
HMTP: 2-Hydroxy-4-methyltetrahydropyrane
*²Recovery rate relative to the amount of the charged rhodium.

EXAMPLE 10

Into an autoclave, 60 ml of 1-eicosene, 60 ml of toluene, 28.6 mg of Rh(acac)(CO)$_2$ and 6 mols, per mol of rhodium atom, of (n—C$_{18}$H$_{37}$)$_3$P were charged, and the hydroformylation reaction was conducted under the same reaction pressure and reaction temperature as in Example 9 for 2 hours. The results of the gas chromatography analysis of this reaction solution were as follows: conversion of 1-eicosene: 97.7 mol %, and yield of formed aldehyde: 95.5 mol %.

Then, to the reaction solution thus obtained, 500 ml of acetonitrile deaerated with argon was added under stirring, whereby a rhodium complex and free (n—C$_{18}$H$_{37}$)$_3$P started to precipitation together with a part of the formed product. The mixture was left to stand in this state for 2 hours, and then subjected to solid-liquid separation by means of a 0.2$\mu$ membrane filter. The amount of rhodium recovered as the solid complex after the separation were 99.2% relative to the charged rhodium.

Then, using the entire amounts of the recovered rhodium complex and free (n—C$_{18}$H$_{37}$)$_3$P, the hydroformylation reaction and precipitation treatment were conducted under the same conditions as the first reaction, whereby the conversion of 1-eicosene was 97.5 mol %, the yield of aldehyde was 95.7 mol %, and the recovery rate of rhodium by precipitation was 99.1%.

EXAMPLE 11

Into a 200 ml autoclave, 60 ml of 1-hydroxy-2,7-octadiene (hereinafter referred to simple as "1-HOD"), 5 ml of n-tetradecane, 15.6 mg of Rh(acac)(CO)$_2$ and 6 equivalent, relative to rhodium, of (n—C$_{18}$H$_{37}$)$_3$P were charged, and then the reaction was conducted under a pressure of 8 kg/cm$^2$G of H$_2$/CO (1/1) at a temperature of 110° C. for 3 hours.

With respect to the reaction solution thereby obtained, the concentration of the product was measured by gas chromatography (column: CBP1 capillary: 0.25$\phi \times$ 50 m, manufactured by Shimazu Corporation), whereby the conversion of 1-HOD was 89.2 mol %, and the yield of the total formed aldehyde was 81.0 mol %. To the entire amount of this reaction solution, the precipitation treatment was conducted in the same manner as in Example 1 except that 200 ml of acetonitrile was added as a poor solvent, and the mixture was cooled to 0° C. and left to stand for one day, whereby 99.3% of rhodium relative to the charged rhodium was recovered as the solid complex.

Then, using the entire amounts of the recovered complex and free (n—C$_{18}$H37)$_3$P, the hydroformylation reaction and precipitation treatment were conducted under the same conditions as in the first reaction, whereby the conversion of 1-HOD was 89.3 mol %, the yield of the total formed aldehyde was 81.9 mol %, and 99.1% of rhodium relative to the charged rhodium was recovered as the solid complex.

EXAMPLE 12

Into a stainless steel top and bottom agitation type autoclave having an internal capacity of 200 ml, 55 ml of 1-octene, 5 ml of toluene and 14.3 mg of Rh(acac)-(CO)$_2$ were charged under a nitrogen atmosphere. Further, the interior of the autoclave was substituted three times with 10 kg/cm$^2$G of nitrogen gas, and the pressure was returned to atmospheric pressure. Then, the temperature was raised to 120° C.. After the temperature reached 120° C., H$_2$/CO (1/1) gas was injected into the autoclave so that the total pressure became 100 kg/cm$^2$G, to initiate the reaction, and the reaction was continued for one hour. The water gas consumed during the reaction was supplemented from the reservoir via a secondary pressure controlling valve so that the pressure was maintained at a level of 100 kg/cm$^2$G.

After the reaction, the reaction solution was withdrawn under an argon atmosphere, and 5 mols, per mol of rhodium atom, of (n—C$_{18}$H$_{37}$)$_3$P was added thereto to form a complex. Further, a part of the reaction solution was analyzed by gas chromatography (column: Thermon-3000 capillary: 0.25$\phi \times$50m) to measure the concentration of the product.

Then, to the above reaction solution, 200 ml of acetonitrile deaerated with argon was added, and the mixture was cooled to a temperature of from 4° to 5° C., and maintained in this state for about 3 hours. The precipitated rhodium complex and free (n—C$_{18}$H$_{37}$)$_3$P were subjected to filtration under reduced pressure by means of a 0.2$\mu$ membrane filter for solid-liquid separation. With respect to rhodium dissolved in the filtrate after the precipitation treatment, the rhodium analysis was conducted by means of a Zeeman type atomic absorption measuring device.

On the other hand, the recovered solid complex was further vacuum-dried at room temperature, and then 55 ml of 1-octene containing 1-octene peroxide, was added and the mixture was stirred at room temperature for 30 minutes. Then, the mixture was cooled to a temperature of 5° C. to −10° C., whereupon precipitated (n—C$_{18}$H$_{37}$)$_3$P=O was separated by filtration. Then, 5 ml of toluene was added and charged again into an autoclave.

The above series of operations was repeated three times, and the results are shown in Table 3.

TABLE 3

| Number of times of the reaction | Conversion of 1-octene (mol %) | Yield of aldehyde (mol %) | Recovery rate of Rh by precipitation (%) |
|---|---|---|---|
| First time | 97.8 | 97.2 | 99.7 |
| 2nd time | 97.0 | 96.1 | 99.2 |
| 3rd time | 97.0 | 96.3 | 99.6 |

According to the present invention, Group VIII metal solid complex can efficiently be recovered from an organic compound-containing solution containing a Group VIII metal complex. Its value for industrial application is particularly high in that it is thereby possible to efficiently recover a valuable Group VIII noble metal complex as a solid complex. Further, the catalyst for a hydroformylation reaction can be recovered efficiently and in an active state by a simple operation and can be recycled to the reaction system, whereby the hydroformylation reaction can advantageously be conducted on an industrial scale. The industrial value of the present invention is very high particularly when a valuable Group VIII noble metal complex catalyst is employed.

What is claimed:

1. A method for recovering a Group VIII metal solid complex from an organic compound-containing solution containing a Group VIII metal complex, wherein the Group VIII metal complex is precipitated in the presence of a trialkyl phosphine of the following formula (I):

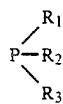

(I)

wherein each of $R_1$, $R_2$ and $R_3$ is an alkyl group and they may be the same or different from one another, and the sum of the carbon numbers of $R_1$, $R_2$ and $R_3$ is at least 42.

2. The method according to claim 1, wherein the Group VIII metal complex is a complex containing a metal selected from the group consisting of Fe, Co, Ni, Ru, Rh, Pd, Os, Ir and Pt, having at least one exchangeable ligand coordinated on the metal and being soluble in the organic compound-containing solution.

3. The method according to claim 2, wherein the ligand is selected from the group consisting of phosphines, phosphites, olefins, nitriles, isonitriles, nitrogen-containing compounds, $\beta$-diketones, $\beta$-ketoesters and carbon monoxide.

4. The method according to claim 1, wherein the concentration of the Group VIII metal complex in the organic compound-containing solution is from 1 mg to 100 g per liter of the solution, as calculated by weight of the metal atoms.

5. The method according to claim 1, wherein each of the three alkyl groups for $R_1$, $R_2$ and $R_3$ of the trialkylphosphine of the formula (I) has at least 10 carbon atoms.

6. The method according to claim 1, wherein each of the three alkyl groups for $R_1$, $R_2$ and $R_3$ of the trialkylphosphine of the formula (I) has at least 16 carbon atoms.

7. The method according to claim 1, wherein the trialkylphosphine of the formula (I) is selected from the group consisting of tri-n-tetradecylphosphine, tri-n-pentadecylphosphine, tri-n-hexadecylphosphine, tri-n-octadecylphosphine, tri-n-eicosylphosphine, tri-n-docosylphosphine, di-n-dodecyl-n-octadecylphosphine, di-n-tetradecyl-n-octadecylphosphine and di-n-hexadecyl-n-decylphosphine.

8. The method according to claim 1, wherein the Group VIII metal complex is precipitated in the presence of at least 1 mol of the trialkylphosphine of the formula (I) per gram atom of the Group VIII metal dissolved in the organic compound-containing solution.

9. The method according to claim 1, wherein the precipitation is conducted in the presence of a solvent inert to the Group VIII metal complex.

10. The method according to claim 9, wherein the solvent is selected from the group consisting of methanol, ethanol, propanol, n-butyl alcohol, acetonitrile and dimethylformamide.

11. The method according to claim 1, wherein the precipitation treatment is conducted at a temperature of from $-78°$ to $80°$ C.

12. The method according to claim 1, wherein the precipitated Group VIII metal solid complex is separated and recovered by solid-liquid separation.

13. A hydroformylation method for producing a hydroformylated product by reacting an olefinic compound with carbon monoxide and hydrogen in the presence of a Group VIII metal complex catalyst, wherein at least a part of the hydroformylation reaction solution is withdrawn and subjected to precipitation treatment in the presence of a trialkylphosphine of the following formula (I):

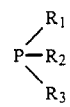

(I)

wherein each of $R_1$, $R_2$ and $R_3$ is an alkyl group and they may be the same or different from one another, and the sum of the carbon numbers of $R_1$, $R_2$ and $R_3$ is at least 42, to precipitate, separate and recover the Group VIII metal complex catalyst, which is recycled to the hydroformylation reaction zone.

14. The method according to claim 13, wherein the hydroformylation reaction is conducted in the presence of a solvent inert to the hydroformylation reaction.

15. The method according to claim 14, wherein the solvent is selected from the group consisting of aromatic hydrocarbon compounds, ketones, ethers and esters.

16. The method according to claim 13, wherein each of the three alkyl groups for $R_1$ $R_2$ and $R_3$ of the trialkylphosphine of the formula (I) has at least 10 carbon atoms.

17. The method according to claim 13, wherein each of the three alkyl groups for $R_1$, $R_2$ and $R_3$ of the trialkylphosphine of the formula (I) has at least 16 carbon atoms.

18. The method according to claim 13, wherein the trialkylphosphine of the formula (I) is selected from the group consisting of tri-n-tetradecylphosphine, tri-n-pentadecylphosphine, tri-n-hexadecylphosphine, tri-n-octadecylphosphine, tri-n-eicosylphosphine, tri-n-docosylphosphine, di-n-dodecyl-n-octadecylphosphine, di-n-tetradecyl-n-octadecylphosphine and di-n-hexadecyl-n-decylphosphine.

19. The method according to claim 13, wherein the Group VIII metal complex catalyst is precipitated in the presence of from 0.5 to 500 mols of the trialkylphosphine of the formula (I) per gram atom of the Group VIII metal dissolved in the solution.

20. The method according to claim 13, wherein the Group VIII metal complex catalyst is precipitated in the presence of from 1 to 100 mols of the trialkylphosphine of the formula (I) per gram atom of the Group VIII metal dissolved in the solution.

21. The method according to claim 13, wherein the precipitation treatment is conducted in the presence of a solvent inert to the Group VIII metal complex catalyst.

22. The method according to claim 21, wherein the solvent is selected from the group consisting of methanol, ethanol, propanol, n-butyl alcohol, acetonitrile and dimethylformamide.

23. The method according to claim 13, wherein the precipitation treatment is conducted at a temperature of from $-78°$ to $80°$ C.

24. The method according to claim 13, wherein the precipitation treatment is conducted at a temperature of from $-20°$ to $50°$ C.

25. The method according to claim 13, wherein the reaction temperature for the hydroformylation reaction is within a range of from room temperature to $200°$ C.

26. The method according to claim 13, wherein the reaction pressure for the hydroformylation reaction is within a range of from atmospheric pressure to 200 atm.

27. A hydroformylation product by reacting an olefinic compound with carbon monoxide and hydrogen in the presence of a Group VIII metal complex catalyst having an organic compound as a ligand, wherein as the organic phosphorus compound, a trialkylphosphine of the following formula (I):

wherein each of $R_1$, $R_2$ and $R_3$ is an alkyl group and they may be the same or different from one another, and the sum of the carbon numbers of $R_1$, $R_2$ and $R_3$ is at least 42, is used, and at least a part of the hydroformylation reaction solution is withdrawn and subjected to precipitation treatment to precipitate, separate and recover the Group VIII metal complex catalyst, which is recycled to the hydroformylation reaction zone.

* * * * *